United States Patent [19]

Potter et al.

[11] Patent Number: 5,229,365
[45] Date of Patent: Jul. 20, 1993

[54] ENDOCRINE CELL STIMULATION BY NEUROTROPHIC AGENTS

[75] Inventors: Huntington Potter, Boston; Michel Polak, Cambridge; Bernd Seilheimer, Brookline, all of Mass.

[73] Assignee: President and Fellows of Harvard College, Cambridge, Mass.

[21] Appl. No.: 700,599

[22] Filed: May 15, 1991

[51] Int. Cl.$^5$ ................ A61K 37/02; A61K 35/12
[52] U.S. Cl. .......................... 514/12; 514/8; 514/21
[58] Field of Search .................. 514/12, 8, 21

[56] References Cited

PUBLICATIONS

Castano and Eisenbarth, Annu. Rev. Immunol. 8:647–679 (1990).
Schneyer and Humphreys-Beher, J. Oral. Pathol. 17:250–256 (1988).
Le Douarin, Cell 53:169–171 (1988).
Alpert et al., Cell 53:295–308 (1988).
Teitelman, Developmental Biology 142:368–379 (1990).
Ernfors et al., Neuron 5:511–526 (1990).
Yada, et al, Journal of Biological Chemistry 264:2455–2462 (1989).
Zawalich, et al., Endocrinology 125:2400–2406 (1989).
Santos and Rojas, FEBS Letters 249:411–417 (1989).
Edwards et al Cell, vol. 58, pp. 161–170 Jul. 14, 1989.
Levi-Montalcini, Science 237:1154–1162 (1987).

Primary Examiner—Michael G. Wityshyn
Assistant Examiner—Choon Koh
Attorney, Agent, or Firm—Hamilton, Brook, Smith & Reynolds

[57] ABSTRACT

The disclosure relates to the stimulation of an endocrine cell, in particular a pancreatic cell or its precursor, to grow and divide upon exposure to a neurotrophic agent such as nerve growth factor, laminin or both.

5 Claims, No Drawings

ENDOCRINE CELL STIMULATION BY NEUROTROPHIC AGENTS

Government Funding

This invention was partially supported by the U.S. Government and the government has certain rights to the invention.

BACKGROUND OF THE INVENTION

Diabetes mellitus is the most common endocrine disease. The disease is characterized by metabolic abnormalities; by long-term complications involving the eyes, kidneys, nerves and blood vessels; and by a lesion of the basement membranes demonstrable by electron microscopy.

Diabetes mellitus can be broadly classified into two groups, insulin-dependent (IDDM) and non-insulin-dependent (NIDDM). IDDM patients require insulin therapy. It is difficult to maintain a normal blood sugar level throughout the course of a day, even if multiple injections or infusion pumps are used. It is even more difficult to maintain a normal blood sugar level utilizing traditional insulin therapy given as one or two injections per day.

A method for treating diabetes mellitus by stimulating the body's own insulin producing cells would, at least in part, overcome the need for insulin therapy in IDDM patients.

SUMMARY OF THE INVENTION

The subject invention relates to a method for stimulating the differentiation of endocrine or exocrine cells (e.g., pancreatic beta cells) by administering an effective amount of a neurotrophic agent. The ability to induce the differentiation of pancreatic beta cells into mature cells which respond to glucose levels by altering the rate of insulin production offers a new approach to the treatment diabetes mellitus.

DETAILED DESCRIPTION OF THE INVENTION

The subject invention is based on the discovery that cells of non-neuronal origin can be stimulated to differentiate by treatment with a neurotrophic agent. In particular, it has been shown that pancreatic beta cells, which are endocrine cells, are induced to differentiate by nerve growth factor (NGF) or laminin and that there is a synergistic effect of NGF and laminin on the ability of pancreatic beta cells to express spikes and to aggregate. This discovery offers a new approach to the treatment of diabetes mellitus, as well as of other endocrine dysfunction.

Pancreatic beta cells are the endocrine cells which secrete insulin in response to elevated glucose levels. Tumors of pancreatic beta cells can be grown in tissue culture and, therefore, provide a good model system for the study of the intracellular events which result in the phenotype which is characteristic of diabetes mellitus.

As described herein, cells of non-neuronal origin undergo observable, identifiable changes in response to contact with a neurotrophic factor and, thus, the effect is readily detectable. For example, prior to contact or treatment with NGF (i.e. in their non-differentiated state), pancreatic beta cells are relatively small and round. After contact with NGF, however, these cells send out cellular processes (spikes) including at their termini the growth-cone like structures which characterize the processes of neuronal cells. This is surprising because experimental evidence strongly suggests that the cells of the pancreas are of non-neuronal developmental origin. That is, they are not derived from the neural crest.

The Exemplification which follows clearly demonstrates that pancreatic beta cells, particularly those in a relatively early stage of development, are induced to differentiate upon treatment with an appropriate amount of a neurotrophic agent. A neurotrophic agent is a substance which induces the growth and/or differentiation of neurons. Well known examples of such agents include nerve growth factor (NGF), laminin, brain derived neurotrophic factor (BDNF), neurotrophic factor 3 (NT3) and cholinergic differentiation factors such as those found in conditioned medium of heart cells. Additional neurotrophic agents are being identified at a rapid rate and any such agent can be tested for its effect on pancreatic beta cells, as described herein, by routine experimentation.

The induction of differentiation in pancreatic beta cells is useful both in vivo and in vitro. In vivo, for example, a neurotrophic agent, or agents, can be administered (e.g., intravenously) in a pharmaceutically acceptable carrier. The administration of an effective amount (as determined empirically) is anticipated to induce beta cells to divide and replace themselves or to induce beta cell precursors to further differentiate to produce more beta cells, as well as to cause concomitant development of glucose sensitivity in the differentiated cells. As the destruction of insulin producing cells is known to be an autoimmune disfunction, the therapy described above may best be carried out in combination with an immunosuppressive regimen in which an immunosuppressant (e.g., cyclosporin A) is given in sufficient quantity to prevent the continuing autoimmune destruction of beta cells.

In vitro, pancreatic beta cells can be treated with a wide variety of neurotrophic agents and analyzed for their effect on cellular differentiation. This method can be used to identify neurotrophic agents useful for in vivo administration, and also as a basic research model for the study of the molecular basis of diabetes.

The invention disclosed herein is not limited to the stimulation of differentiation in pancreatic beta cells or their precursors. Any endocrine or exocrine cell of non-neuronal origin can be tested, using only routine experimentation, for differentiation potential under the influence of a neurotrophic agent. That is, a cell of apparent non-neuronal origin is contacted with a neurotrophic agent (or a combination of neurotrophic agents) and its appearance is assessed as an indication of the effect (or lack of effect) of the factor(s). A change from its typical non-differentiated appearance to one in which neurite-like processes are present is indicative of an effect of the neurotrophic agent. Alternatively, the presence or absence of a neurotrophic agent receptor (such as the NGF receptor) can be used to identify and isolate cells for which the present method of stimulating differentiation is operable.

The present invention will now be further illustrated by the following Exemplification, which is not intended to be limiting in any way.

Exemplification

Assessment of the Effect of Neurotrophic Agents on Cells of Non-Neuronal Origin (Insulin-Secretion Cells)

A subclone (RINm5F) of a continuous clonable rat cell line was used in this study. This cell line contains and secretes predominantly insulin and, to a lesser degree (as compared to the parental line and other subclones), glucagon and somatostatin. Like fetal rat beta cells, RINm5F cells do not respond to glucose by increasing their insulin secretion. A second cell line, betaTC3, is a non-clonal cell line derived from a transgenic mouse SV40-induced insulinoma. BetaTC3 cells are more differentiated and respond to glucose by secreting insulin. Thus, RINm5F and betaTC3 represent the early and middle-late stages respectively of pancreatic beta cell differentiation.

RINm5F and betaTC3 cell lines were cultured in RPMI1640 (5% fetal calf serum for the RINm5F cells and 10% fetal calf serum for the betaTC3 cell). Three days before the experiment they were transferred to defined, serum free medium, containing insulin (5 $\mu$g/ml), transferrin (10 $\mu$g/ml), sodium-selenite (30 nM), putrescine (100 $\mu$M), progesterone (20 nM) and biotin (30 nM) which enabled the cells to grow for at least two weeks. PC12 pheochromocytoma cells were used as a positive control for the effect of NGF. The cells were split using EDTA and plated at low density on poly-L-lysine coated plastic culture dishes. NGF (100 ng/ml) and laminin (10 $\mu$g/ml), either alone or in combination, were added to the culture. Medium and factors were renewed every 48 hours. NGF with an anti-NGF antibody (500 ng/ml) was used as a control.

Cells cultured in defined medium alone, or in the presence of BSA, remained round during 3 to 5 days and then lifted off the dish. 52 to 65% of RINm5F cells cultured either with NGF or with laminin or both displayed cellular projections (spikes) in contrast to typical small round cells observed in define medium on poly-L-lysine coated culture dishes. The presence of the anti-NGF antibody abolished the effect of NGF. BetaTC3 remained round in the presence of NGF, but extended processes in the presence of laminin. These processes were also observed in the presence of serum for RINm5F cells and betaTC3 cells.

These processes were assayed for the presence of neurofilaments both by immunocytochemical analysis using RINm5F cells plated on poly-L-lysine coated glass coverslips at day 4. Coverslips were washed in DPBS and the cells permeabilized in cold ethanol for 1.5 min, then washed again. The coverslips were then incubated with a mouse monoclonal antibody against the 160 kD component of the neurofilament diluted 1 to 10 in DPBS, 10% horse serum and 0.1% BSA for one hour. After a washing step the secondary antibody (dilution 1 to 250), a fluoresceinated anti-mouse conjugate was added for 1 hour in the dark. For negative controls, the first antibody was omitted. The PC12 cells were utilized as positive control. Northern blot analysis can be carried out by conventional methods with a probe that recognizes the three components of the neurofilament to confirm the immunocytochemical results.

Thus, the RINm5F cells are able to extend cytoplasmic processes under the influence of NGF. Because these processes contain neurofilament, a protein specific to neurons, RINm5F cells can be described as neurite-like. In contrast, the betaTC3 are not able to display neurites in response to NGF but grow neurofilament positive processes under the influence of laminin.

NGF is known to bind a cell surface receptor, thereby signaling the onset of specific intracellular processes. Two types of NGF receptors, a high and low affinity receptor, have been described in the literature. It has been reported that the tyrosine kinase protein encoded by the trk oncogene is either a high affinity receptor for NGF or combines with the low affinity receptor (which alone does not transduce the signal) to form a high affinity receptor with full biological activity. The trk protein has been found only on neural crest derived sensory neurons, sympathetic neurons, central cholinergic neurons and the neuronal pheochromocytoma cell line, PC12.

A search for biochemical evidence of NGF binding to a high affinity receptor on RINm5F cells was carried out by assaying the induction of c-fos gene. C-fos transcriptional activity is known to increase in response to NGF in PC12 cells. When NGF was added to RINm5F cells, c-fos mRNA increased thereby suggesting that RINm5F cells do, in fact, carry a high affinity NGF receptor.

PCR amplification of the non-tyrosine kinase domain of the trk cDNA in RINm5F cells, using primers designed from the known sequence of the mouse trk gene, can used to generate trk specific probes. Such probes can be used to determine the presence of the trk gene in the RINm5F cells as a further indication of the presence of high affinity NGF receptors in these non-neuronal cells.

Low affinity NGF receptor has previously been found on some non-neuronal cells, for example the Sertoli cells of rat testis by in situ hybridization. By immunocytochemistry we showed that the low affinity NGF receptor was present on the RINm5F cells but not on the beta TC3 cells, consistent with their different responses to the NGF.

Cultured cells were grown on poly-L-lysine coated glass coverslips and treated as described in the immunocytochemistry protocol described above except that the permeabilization step was omitted. RINm5F, but not betaTC3 cells, stained with a mouse monoclonal antibody against the low affinity NGF receptor (Boehringer). This result was confirmed Northern blot analysis using a probe synthesized by polymerase chain reaction (PCR) amplification of the portion of the low affinity NGF receptor cDNA coding for the extracellular domain of the protein.

Equivalents

Those skilled in the art will know, or be able to ascertain using no more than routine experimentation, many equivalents to the specific embodiments of the invention described herein. These and all other equivalents are intended to be encompassed by the following claims.

We claim:

1. A method for stimulating the differentiation of a population of pancreatic beta cells or their precursors comprising:
   a) identifying a differentiation-stimulating neurotrophic agent by:
      i) growing a test group of pancreatic beta cells in culture;
      ii) contacting the test group with an appropriate amount of at least one neurotrophic agent; and iii) identifying a neurotrophic agent which is effective in stimulating said differentiation by the presence of differentiated pancreatic beta cells in the test group; and b) contacting the population of pancreatic beta cells or their precursors with an effective amount of the differentiation-stimulating neurotrophic agent of step a).

2. A method for stimulating the differentiation of a population of endocrine or exocrine cells of non-neuronal origin comprising:

a) identifying a differentiation-stimulating neurotrophic agent by:
  i) growing a test group of endocrine or exocrine cells in culture;
  ii) contacting the test group with an appropriate amount of at least one neurotrophic agent; and
  iii) identifying a neurotrophic agent which is effective in stimulating said differentiation by the presence of differentiated endocrine or exocrine cells in the test group; and b) contacting the population of endocrine or exocrine cells with an effective amount of the differentiation-stimulating neurotrophic agent of step a).

3. A method of claim 2 wherein the neurotrophic agent is nerve growth factor or laminin.

4. A method for identifying endocrine or exocrine cells which respond to contact with at least one neurotrophic agent by differentiating comprising:
  a) growing said cells in culture;
  b) contacting said cells with an appropriate amount of at least one neurotrophic agent; and
  c) identifying those cells which respond to the neurotrophic agent by differentiating.

5. A method for stimulating the differentiation of pancreatic beta cells or their precursors comprising contacting the cells with an effective amount of nerve growth factor or laminin.

* * * * *